United States Patent [19]

Chang

[11] Patent Number: 4,788,325

[45] Date of Patent: Nov. 29, 1988

[54] CONVERSION OF AN ALLYLIC ETHER TO ITS CORRESPONDING CARBONYL COMPOUND

[75] Inventor: Biau-Hung Chang, West Chester, Ohio

[73] Assignee: National Distillers and Chemical Corporation, New York, N.Y.

[21] Appl. No.: 55,393

[22] Filed: May 29, 1987

[51] Int. Cl.⁴ .............................................. C07C 45/51
[52] U.S. Cl. .................................... 560/174; 568/405; 568/485; 568/387; 568/342; 568/311; 568/428; 568/451; 568/444; 558/440
[58] Field of Search ............... 568/381, 342, 311, 328, 568/444, 451, 429, 405, 415; 560/124; 558/440

[56] References Cited

U.S. PATENT DOCUMENTS 3,830,846 8/1974 Duembgen et al. ................. 560/174
4,140,865 2/1979 Fernholz et al. ................... 568/387
4,297,517 10/1981 Van Broekhoven et al. ...... 568/485

FOREIGN PATENT DOCUMENTS 630926 10/1949 United Kingdom ................ 568/485

Primary Examiner—James H. Reamer
Attorney, Agent, or Firm—Kenneth D. Tremain

[57] ABSTRACT

A process for making a carbonyl-containing compound is disclosed. In this process an allylic ether is contacted with water in the presence of a cobalt-containing material under an atmosphere of carbon monoxide gas.

27 Claims, No Drawings

CONVERSION OF AN ALLYLIC ETHER TO ITS CORRESPONDING CARBONYL COMPOUND

BACKGROUND OF THE DISCLOSURE

1. Field of the Invention

The present invention is directed to a process for converting an allylic ether to its corresponding carbonyl compound. More particularly, the present invention is directed to a process for hydrolyzing an allylic ether to its corresponding aldehyde in the presence of a cobalt-containing material.

2. Background of the Prior Art

New synthetic routes to synthesize commercially important organic acids have long attracted the attention of organic chemists. New, better and more efficient routes to such commercial products are continually being developed. One attractive means to the production of these acids is postulated to be through the formation of aldehyde intermediates which can be easily oxidized to the corresponding acid. For instance, azelaic acid can be formed by this scheme from alkyl 9-oxononanoates. Therefore, new processes for the development of such aldehyde intermediates are of significant commercial importance.

A process for producing an aldehyde by hydrolysis of an allylic ether is known in the art. Japanese Patent Application No. 46-15658 discloses such a process. In that process an allylic ether is contacted with water in the presence of a ruthenium compound, preferably ruthenium chloride, under a nitrogen atmosphere. Although this process represents an advance in the art, it is inefficient. The total yield to the desired aldehyde is only between 40 and 45%. Moreover, to obtain this relatively low yield, a long reaction time, about two hours, is required.

The above remarks establish the need in the art for a new process for producing aldehyde compounds from an allylic ether which produces higher yields of the desired product over shorter periods of time. Such a process could be commercially exploited to develop new aldehydes useful in the synthesis of commercially important organic compounds.

BRIEF SUMMARY OF THE INVENTION

A new process has now been developed which provides a method for obtaining a carbonyl compound selected from the group consisting of aldehydes and ketones, having utility as an intermediate, obtained in a very high yield and requiring a very short reaction time.

In accordance with the present invention a process is provided for making a carbonyl-containing compound selected from the group consisting of aldehydes and ketones. In this process an allylic ether is contacted with water in the presence of a cobalt-containing material under an atmosphere of carbon monoxide gas.

DETAILED DESCRIPTION

The process of the present invention is directed to the formation of carbonyl-containing compounds selected from the group consisting of aldehydes and ketones by the hydrolysis of an allylic ether. In particular, this process involves contacting an allylic ether with water in the presence of a cobalt-containing material under an atmosphere of carbon monoxide gas.

Allylic ethers within the contemplation of the present invention are characterized by the structural formula $$R^1-CH=CH-CH(R^3)OR^2 \qquad (I)$$

where $R^1$ and $R^3$ are the same or different and are hydrogen or a cyclic or acyclic hydrocarbyl group containing up to about 15 carbon atoms which may be substituted with a carboxylate group, a carbonyl group, a nitrile group, an ether group or mixtures thereof; and $R^2$ is a cyclic or acyclic hydrocarbyl containing up to about 12 carbon atom.

More preferably, the allylic compound having the structural formula (I) is characterized by $R^1$ being hydrogen or a cyclic or acyclic hydrocarbyl group containing up to about 10 carbon atoms which may be substituted with a carboxylate group, a carbonyl group, a nitrile group, an ether group or mixtures thereof; $R^2$ is a cyclic or acyclic hydrocarbyl group containing up to about 8 carbon atoms; and $R^3$ is hydrogen.

Still more preferably, $R^1$ is hydrogen, $C_1$-$C_{10}$ alkyl, $C_1$-$C_{10}$ alkenyl, $C_6$-$C_{10}$ aryl or $C_7$-$C_{10}$ aralkyl, $C_1$-$C_{10}$ alkyl substituted with a carboxylate, carbonyl, nitrile or ether group, $C_1$-$C_{10}$ alkenyl substituted with a carboxylate, carbonyl, nitrile or ether group, $C_6$-$C_{10}$ aryl substituted with a carboxylate, carbonyl, nitrile or ether group or $C_7$-$C_{10}$ aralkyl substituted with a carboxylate, carbonyl, nitrile or ether group; $R^2$ is $C_1$-$C_8$ alkyl, phenyl or $C_7$-$C_8$ aralkyl; and $R^3$ is hydrogen.

Even more preferably, $R^1$ is hydrogen or $C_1$-$C_{10}$ alkyl substituted with a carboxylate, carbonyl, nitrile or ether group; $R^2$ is $C_1$-$C_2$ alkyl; and $R^3$ is hydrogen.

In a particularly preferred embodiment of the present application the allylic ether is methyl 9-methoxy-7-nonenoate. That is, the compound having the structural formula (I) is defined by $R^1$ being pentyl substituted with a carboxylate group and $R^2$ being methyl.

The hydrolysis of the allylic ether takes place in the presence of a cobalt-containing material which acts as a catalyst. Any cobalt-containing material including cobalt metal, a cobalt compound or a cobalt coordination complex may be utilized in the process of the instant invention. Of the cobalt-containing materials within the contemplation of the present application, cobalt salts and cobalt coordination complexes are preferred. Of the cobalt salts within the contemplation of the present invention, cobalt halides, cobalt carbonate and cobalt carboxylates are particularly preferred. Of the cobalt coordination complexes, dicobalt octacarbonyl, $Co_2(CO)_8$, is preferred. Of the above mentioned preferred compounds, dicobalt octacarbonyl and cobalt halides are particularly preferred. The cobalt-containing material most preferred for use in the process of the present application is dicobalt octacarbonyl.

In addition to the necessity of a cobalt-containing catalyst, the hydrolysis reaction requires an atmosphere of carbon monoxide. The carbon monoxide gas, additionally, provides the bulk of the pressure under which the reaction occurs. In a preferred embodiment, a second gas, also contributing to the pressure of the reaction, hydrogen gas, is utilized. When hydrogen gas is present, it is preferably provided in a concentration of about 1% to about 8% by volume, based on the volume of the carbon monoxide present in the process.

In addition to a cobalt-containing material under an atmosphere of carbon monoxide, which may include hydrogen gas, it is preferred that the process of the present invention take place in the presence of an aprotic solvent. Those skilled in the art are aware that an aprotic solvent is defined as a solvent that does not function as a proton donor. Among the aprotic solvents within the contemplation of the present invention are ethers, esters, ketones, hydrocarbons, chlorinated compounds, nitriles and carbonates. Of these aprotic solvents, ethers, esters and hydrocarbons are preferred. Especially preferred are ethers and hydrocarbons. Of the ether and hydrocarbon aprotic solvents within the contemplation of the present invention, those particularly preferred are $C_6$-$C_{10}$ alkanes, tetrahydrofuran and dioxanes. The aprotic solvents most preferred for use in the process of the present application are tetrahydrofuran or 1,4-dioxane.

The unique process of the present application, described above, is conducted at a temperature in the range of between about 90° C. and about 220° C. More preferably, the temperature at which the process of this invention occurs is in the range of between about 150° C. and about 200° C. Most preferably, the temperature of the instant process is in the range of between about 160° C. and about 190° C.

The pressure at which this process occurs is in the range of between about 500 psig and about 4000 psig. More preferably, the pressure at which this hydrolysis process occurs is in the range of between about 1000 psig and 3000 psig. Still more preferably, the pressure of the process of this reaction is in the range of between about 1000 psig and 2000 psig. As suggested earlier, this pressure is provided by the pressure of the carbon monoxide gas. In the preferred embodiment wherein hydrogen gas is present, along with carbon monoxide gas, the pressure of the process is imparted by the sum of the partial pressures of the carbon monoxide gas and the hydrogen gas.

The duration of the process is in the range of between about 1 minute and 4 hours. More preferably, the period over which this process occurs is in the range of between about 10 minutes and about 2 hours. Most preferably, the process occurs over a period of between about 20 minutes and about 1 hour.

The hydrolysis of the allylic ether usually results in the formation of an aldehyde. However, the preferred class of allylic ethers, the compounds having the structural formula (I) results in the formation of a carbonyl-containing compound having the structural formula,

where $R^1$ and $R^3$ have the same meanings as those given for compounds having structural formula (I). Typical of hydrolysis reactions, a second product, a hydroxyl compound having the structural formula, $$R^2OH \qquad (III)$$

where $R^2$ has the same meanings as those given above for the allylic compound having the structural formula (I), is formed.

Preferred carbonyl-containing compounds characterized by structural formula (II) have the same meanings of $R^1$ and $R^3$ as the preferred allylic ethers defined by structural formula (I). Similarly, the more preferred and most preferred carbonyl-containing compounds, defined by structural formula (II), are those having the same meanings of $R^1$ and $R^3$ as the meanings of $R^1$ and $R^3$ in the more preferred and most preferred embodiments of the allylic ether having structural formula (I).

In that preferred allylic ethers of the present invention, defined by structural formula (I), have a meaning of $R^3$ of hydrogen establish that the preferred product of the process of the present invention is an aldehyde having the structural formula

It follows then that the more preferred, still more preferred and most preferred meanings of $R^1$ of the allylic ether starting material are representative of the more preferred, still more preferred and most preferred meanings of $R^1$ in the aldehyde product, defined by structural formula (IV) of this process. Of particular interest is the product alkyl n-oxoalkanoate, where n is an integer equal to the number of carbon atoms in the alkanoate. Based on the most preferred meanings of $R^1$ it is apparent that methyl 9-oxononanoate is a particularly preferred aldehyde product of the process of this invention.

The following examples are given to illustrate the scope of the present invention. Because these examples are given for illustrative purposes only, the present invention should not be limited thereto.

EXAMPLE 1

Hydrolysis of Methyl 9-Methoxy-7-Nonenoate in THF 30.0 g. (90.5% pure) methyl 9-methoxy-7-nonenoate (MMNE); 5.4 g. water; 60.0 g. tetrahydrofuran (THF); and 1.80 g. pentamethylbenzene, a gas chromatography standard, were charged into a glass bottle and the contents mixed. The mixture was disposed in a 300 ml. autoclave reactor that had previously been purged with nitrogen gas. Along with this mixture, 0.25 g. dicobalt octacarbonyl, $Co_2(CO)_8$, was separately charged into the reactor from a vial.

The reactor was sealed, purged three times with carbon monoxide and pressured to 40 psig with hydrogen gas. The total pressure was increased to 590 psig by the addition of 550 psig carbon monoxide gas. The reactor was heated to 170° C. and carbon monoxide was added to bring the pressure up to 1000 psig. The reactor was maintained at 170° C. and 1000 psig for 0.5 hour. The reactor was then cooled to room temperature and the product mixture analyzed by gas-liquid chromatography.

It was found that MMNE was completely converted with a selectivity to methyl 9-oxononanoate (MON) of 99%.

EXAMPLES 2-8 AND COMPARATIVE EXAMPLE 1

Hydrolysis of Methyl 9-Methoxy-7-Nonenoate in Polar Solvents

Eight additional runs were made in substantial accordance with the procedure set forth in Example 1. However, each example includes at least one variation in the amount of at least one component charged into the reactor or at least one variation in thermodynamic conditions under which the reaction occurred.

Comparative Example 1 is a comparative example in that the solvent was acetic acid, a protic solvent outside the aprotic solvents of the present invention.

The results of these examples, including percent conversion of MMNE and percent selectivity to MON, are included in Table 1 below. Table 1 includes Example 1 described above.

TABLE 1

| Expt. No. | MMNE*, g. | Solvent | Wt. of Solv., g. | Wt. of Water, g. | Wt. of Co2(CO)8, g. | H2, psig. | CO, psig. | Temp., °C. | Reac. Time, hr. | Conv. of MMNE, % | Selec. to MON, % |
|---|---|---|---|---|---|---|---|---|---|---|---|
| 1 | 30.0 | THF | 60.0 | 5.4 | 0.25 | 40 | 960 | 170 | 0.5 | 100 | 99 |
| 2 | 30.0 | THF | 60.0 | 5.4 | 0.25 | 40 | 960 | 180 | 0.33 | 99 | 99 |
| 3 | 30.0 | THF | 60.0 | 5.4 | 0.10 | 40 | 960 | 170 | 0.5 | 96 | 99 |
| 4 | 30.0 | THF | 60.0 | 5.4 | 0.25 | 0 | 1,000 | 170 | 0.5 | 47 | 90 |
| 5 | 31.3 | THF | 60.0 | 5.4 | 0.25 | 10 | 990 | 170 | 0.5 | 95 | 99 |
| 6 | 30.0 | Acetone | 60.0 | 5.4 | 0.25 | 40 | 960 | 170 | 0.5 | 91 | 70 |
| 7 | 30.0 | 1,4-Dioxane | 50.6 | 5.4 | 0.25 | 60 | 1,440 | 170 | 0.5 | 99 | 99 |
| 8 | 15.0 | Acetonitrile | 50.2 | 5.4 | 0.25 | 40 | 960 | 170 | 1.0 | 89 | 86 |
| CE1 | 30.0 | Acetic Acid | 60.0 | 5.4 | 0.25 | 40 | 960 | 170 | 0.5 | 26 | 31 |

*90.5% pure

EXAMPLE 9

Hydrolysis of Methyl 9-Methoxy-7-Nonenoate in Octane

Example 1 was repeated except that the 60 g. of THF of that example was replaced with 60.0 g. of octane. The mixture was charged into the reactor and processed in accordance with Example 1.

In this case a phase separation of the product mixture was observed. It was found that the top layer contained 0.3 g. MMNE and 7.1 g. MON. The bottom layer contained 0.2 g. MMNE and 16.2 g. MON. This represented an overall yield of 95% MON from MMNE.

EXAMPLE 10

Hydrolysis of Methyl 9-Methoxy-7-Nonenoate in Hexane

Example 9 was repeated except for the replacement of 60.0 g. octane with 60.0 g. hexane. Again, a phase separation was noted in the product mixture. It was found that the top layer contained 0.2 g. MMNE and 7.7 g. MON. The bottom layer contained 0,2 g. MMNE and 17.9 g. MON. This represents an overall yield of MON from MMNE of 99%.

EXAMPLE 11

Hydrolysis of Methyl 9-Methoxy-7-Nonenoate Without a Solvent

The procedure employed in Example 1 was repeated except that the reaction temperature was 180° C., the hydrogen partial pressure was 80 psig, the carbon monoxide partial pressure was 1920 psig, 60.0 g. MMNE and 0.50 g dicobalt octacarbonyl were charged to the reactor and no solvent was present.

The reaction resulted in an MMNE conversion of 98%. The resultant product was a mixture of MON, formed at a selectivity of 68%, and methyl 9,9-dimethoxynonanoate, obtained at a selectivity of 28%.

EXAMPLE 12

Hydrolysis of 8-Methoxy-1,6-Octadiene

A glass bottle was charged with 20.0 g. 8-methoxy-1,6-octadiene; 5.1 g. water; 76.0 g. THF; and 1.80 g. pentamethylbenzene, a gas chromatography standard. The contents of the glass bottle were mixed and added to a nitrogen purged 300 ml. autoclave reactor along with 0.50 g. dicobalt octacarbonyl, separately charged from a vial.

The reactor was sealed, purged three times with carbon monoxide and pressured to 80 psig with hydrogen gas. The total pressure was increased to 1500 psig by the addition of 1420 psig carbon monoxide gas. The reactor was heated to 170° C. and carbon monoxide gas was added to bring the pressure up to 2000 psig.

The reactor was maintained at these conditions for two hours, cooled to room temperature and the product mixture analyzed by means of gas-liquid chromatography. It was found that 63% of the 8-methoxy-1,6-octadiene was converted to a mixture of octenal (selectivity 11%) and octanal (selectivity 21%).

EXAMPLE 13

Hydrolysis of Allyl Ethyl Ether

The procedure of Example 1 was repeated except that the glass bottle was charged with 15.0 g. allyl ethyl ether, instead of 30.0 g. of MMNE; 6.3 g., instead of 5.4 g., of water; and 80.0 g., instead of 60.0 g., of THF. The amount of dicobalt octacarbonyl, the thermodynamic conditions and time of reaction were as in Example 1.

The result of this example was a complete conversion (100%) of the allyl ethyl ether. The product of this conversion was a mixture of propanal (selectivity 70%) and n-propanol (selectivity 20%).

EXAMPLE 14

Hydrolysis of Allyl Phenyl Ether

Example 13 was repeated except that 15.0 g. of allyl phenyl ether replaced the 15.0 g. of allyl ethyl ether of Example 13 and 4.0 g. water was used, instead of the 6.3 g. water of Example 13. Although the thermodynamic conditions of Example 13 were maintained, the time of the reaction was extended to 1 hour, rather than the 0.5 hour duration of Example 13.

The result of this example was a 98% conversion of the allyl phenyl ether to a mixture of propanal (selectivity 72%) and n-propanol (selectivity 2%).

The above embodiments and examples are given to illustrate the scope and spirit of the instant invention. These embodiments and examples will make apparent, to those skilled in the art, other embodiments and examples. These other embodiments and examples are within the contemplation of the present invention. Therefore, the scope of the present invention should be limited only by the appended claims.

What is claimed is:

1. A process for making a carbonyl-containing compound selected from the group consisting of aldehydes and ketones comprising contacting an allylic ether having the structural formula $$R^1-CH=CH-CH(R^3)-OR^2$$

where $R^1$ and $R^3$ are the same or different and are hydrogen or a cyclic or an acyclic hydrocarbyl group containing up to about 15 carbon atoms which may be substituted with a carboxylate group, a carbonyl group, a nitrile group, an ether group or mixtures thereof; and $R^2$ is a cyclic or acyclic hydrocarbyl group containing up to about 12 carbon atoms with water in the presence of a cobalt-containing material under an atmosphere of carbon monoxide gas whereby a carbonyl-containing compound having the structural formula $$R^1-CH_2-CH_2-CR^3(O)$$

where $R^1$ and $R^3$ have the meanings given above is formed.

2. A process in accordance with claim 1 wherein said cobalt-containing material is a cobalt coordination complex or a cobalt salt.

3. A process in accordance with claim 2 wherein said cobalt-containing material is a cobalt carbonyl complex, a cobalt halide, a cobalt carbonate or a cobalt carboxylate.

4. A process in accordance with claim 3 wherein said cobalt-containing material is dicobalt octacarbonyl.

5. A process in accordance with claim 1 wherein $R^1$ is hydrogen or a cyclic or an acyclic hydrocarbyl group containing up to about 10 carbon atoms which may be substituted with a carboxylate group, a carbonyl group, a nitrile group, an ether group or mixtures thereof; $R^2$ is a hydrocarbyl group containing up to about 8 carbon atoms; and $R^3$ is hydrogen.

6. A process in accordance with claim 5 wherein $R^1$ is hydrogen, $C_1$-$C_{10}$ alkyl, $C_1$-$C_{10}$ alkenyl, $C_6$-$C_{10}$ aryl or $C_7$-$C_{10}$ aralkyl, $C_1$-$C_{10}$ alkyl substituted with a carboxylate, carbonyl, nitrile or ether group, $C_1$-$C_{10}$ alkenyl substituted with a carboxylate, carbonyl, nitrile or ether group, $C_6$-$C_{10}$ aryl substituted with a carboxylate, carbonyl or ether group or $C_7$-$C_{10}$ aralkyl substituted with a carboxylate, carbonyl, nitrile or ether group; and $R^2$ is $C_1$-$C_8$ alkyl, phenyl or $C_7$-$C_8$ aralkyl.

7. A process in accordance with claim 6 wherein $R^1$ is hydrogen or $C_1$-$C_{10}$ alkyl substituted with a carboxylate, carbonyl, nitrile or ether group; and $R^2$ is $C_1$-$C_2$ alkyl.

8. A process in accordance with claim 7 wherein $R^1$ is pentyl substituted with a carboxylate group; and $R^2$ is methyl.

9. A process in accordance with claim 1 comprising contacting said allylic ether and said water in the presence of an aprotic solvent.

10. A process in accordance with claim 9 wherein said aprotic solvent is an ether, an ester, a ketone, a hydrocarbon, a chlorinated solvent, a nitrile or a carbonate.

11. A process in accordance with claim 10 wherein said aprotic solvent is an ether or a hydrocarbon.

12. A process in accordance with claim 11 wherein said aprotic solvent is $C_6$-$C_{10}$ alkane, tetrahydrofuran or 1,4-dioxane.

13. A process in accordance with claim 12 wherein said aprotic solvent is tetrahydrofuran or 1,4-dioxane.

14. A process in accordance with claim 1 including the presence of hydrogen gas.

15. A process in accordance with claim 14 wherein said hydrogen gas is present in a concentration of about 1% to about 8% by volume, based on the volume of said carbon monoxide gas.

16. A process in accordance with claim 1 wherein said contact occurs at a temperature in the range of between about 90° C. and about 220° C.; a pressure in the range of between about 500 psig and about 4000 psig; and over a period of about 1 minute to about 4 hours.

17. A process in accordance with claim 16 wherein said contact occurs over a temperature in the range of between about 150° C. and about 200° C.; a pressure of between about 1000 psig and about 3000 psig; and over a period of about 10 minutes to about 2 hours.

18. A process in accordance with claim 17 wherein said temperature is in the range of between about 160° C. and about 190° C.; a pressure in the range of between about 1000 psig and about 2000 psig; and a contact time in the range of between about 20 minutes and about 1 hour.

19. A process for making alkyl 9-oxononanoates comprising contacting an alkyl 9-alkoxy-7-nonenoate with water in the presence of a cobalt-containing material under an atmosphere of carbon monoxide gas.

20. A process in accordance with claim 19 including the presence of an aprotic solvent.

21. A process in accordance with claim 20 including the presence of hydrogen gas, provided in a concentration of about 1% to about 8% by volume, based on the volume of said carbon monoxide gas.

22. A process in accordance with claim 19 wherein said cobalt-containing material is selected from the group consisting of a cobalt coordination complex and a cobalt salt.

23. A process in accordance with claim 22 wherein said cobalt-containing material is dicobalt octacarbonyl.

24. A process in accordance with claim 23 wherein said aprotic solvent is an ether or a hydrocarbon.

25. A process in accordance with claim 24 wherein said aprotic solvent is tetrahydrofuran or 1,4-dioxane.

26. A process in accordance with claim 19 wherein said contact occurs at a temperature in the range of between about 160° C. and about 190° C.; a pressure in the range of between about 1000 psig and about 2000 psig; and over a period of time of between about 20 minutes and 1 hour.

27. A process in accordance with claim 19 wherein said alkyl 9-alkoxy-7-nonenoate is methyl 9-methoxy-7-nonenoate.

* * * * *